(12) United States Patent
Baker et al.

(10) Patent No.: US 7,338,491 B2
(45) Date of Patent: Mar. 4, 2008

(54) SPINAL FIXATION LOCKING MECHANISM

(75) Inventors: Daniel R. Baker, Seattle, WA (US);
Carly A. Thaler, Seattle, WA (US);
Alex E. Kunzler, Issaquah, WA (US);
David T. Stinson, Woodenville, WA (US)

(73) Assignee: Spinefrontier Inc, Beverly, MA (US)

( * ) Notice: Subject to any disclaimer, the term of this patent is extended or adjusted under 35 U.S.C. 154(b) by 34 days.

(21) Appl. No.: 11/086,005

(22) Filed: Mar. 22, 2005

(65) Prior Publication Data

US 2006/0217716 A1 Sep. 28, 2006

(51) Int. Cl.
*A61B 17/56* (2006.01)
(52) U.S. Cl. ............................................. 606/61
(58) Field of Classification Search ............... 606/53, 606/60–61, 72–73
See application file for complete search history.

(56) References Cited

U.S. PATENT DOCUMENTS

| | | | |
|---|---|---|---|
| 4,611,581 A | 9/1986 | Steffee | |
| 4,805,602 A | 2/1989 | Puno et al. | |
| 4,854,311 A | 8/1989 | Steffee | |
| 4,887,596 A | 12/1989 | Sherman | |
| 4,946,458 A | 8/1990 | Harms et al. | |
| 5,113,685 A | 5/1992 | Asher et al. | |
| 5,129,900 A | 7/1992 | Asher et al. | |
| 5,207,678 A | 5/1993 | Harms et al. | |
| 5,261,303 A | 11/1993 | Strippgen | |
| 5,312,404 A | 5/1994 | Asher et al. | |
| 5,360,431 A | 11/1994 | Puno et al. | |
| 5,443,467 A | 8/1995 | Biedermann et al. | |
| 5,466,237 A | 11/1995 | Byrd, III et al. | |
| 5,474,555 A | 12/1995 | Puno et al. | |
| 5,476,463 A | 12/1995 | Boachie-Adjei et al. | |
| 5,507,746 A | 4/1996 | Lin | |
| 5,522,816 A | 6/1996 | Dinello et al. | |
| 5,534,001 A | 7/1996 | Schlapfer et al. | |
| 5,549,608 A | 8/1996 | Errico et al. | |
| 5,554,157 A | 9/1996 | Errico et al. | |
| 5,569,247 A | 10/1996 | Morrison | |
| 5,575,792 A | 11/1996 | Errico et al. | |
| 5,578,033 A | 11/1996 | Errico et al. | |
| 5,584,834 A | 12/1996 | Errico et al. | |

(Continued)

FOREIGN PATENT DOCUMENTS

EP 0878171 A1 11/1998

(Continued)

*Primary Examiner*—Eduardo C. Robert
*Assistant Examiner*—Michael J Araj
(74) *Attorney, Agent, or Firm*—AKC Patents LLC; Aliki K. Collins

(57) ABSTRACT

The present invention relates to a locking mechanism and method of fixation, such as the fixation of a fixation device like a bone screw and of a stabilization device like a rod to the spine. The locking mechanism includes a seat and a locking element. The seat includes a bottom portion configured to receive the fixation device such that a socket of the bottom portion engages part of the fixation device and prevents the fixation device from passing entirely therethrough. The seat further includes a side portion configured to receive the stabilization device and a locking element. The locking element, when fully engaged with the side portion of the seat, causes locking of the relative positions of the fixation device and the stabilization device.

26 Claims, 7 Drawing Sheets

U.S. PATENT DOCUMENTS

| | | | |
|---|---|---|---|
| 5,586,984 A | 12/1996 | Errico et al. | |
| 5,609,593 A | 3/1997 | Errico et al. | |
| 5,609,594 A | 3/1997 | Errico et al. | |
| 5,643,263 A | 7/1997 | Simonson | |
| 5,643,265 A | 7/1997 | Errico et al. | |
| 5,647,873 A | 7/1997 | Errico et al. | |
| 5,672,176 A | 9/1997 | Biedermann et al. | |
| 5,683,392 A | 11/1997 | Richelsoph et al. | |
| 5,688,274 A | 11/1997 | Errico et al. | |
| 5,690,630 A | 11/1997 | Errico et al. | |
| 5,713,898 A | 2/1998 | Stücker et al. | |
| 5,725,527 A | 3/1998 | Biedermann et al. | |
| 5,725,528 A | 3/1998 | Errico et al. | |
| 5,725,588 A | 3/1998 | Errico et al. | |
| 5,728,098 A | 3/1998 | Sherman et al. | |
| 5,733,285 A | 3/1998 | Errico et al. | |
| 5,733,286 A | 3/1998 | Errico et al. | |
| 5,738,685 A | 4/1998 | Halm et al. | |
| 5,741,255 A | 4/1998 | Krag et al. | |
| 5,743,907 A | 4/1998 | Asher et al. | |
| 5,776,135 A | 7/1998 | Errico et al. | |
| 5,782,833 A | 7/1998 | Haider | |
| 5,797,911 A | 8/1998 | Sherman et al. | |
| 5,817,094 A | 10/1998 | Errico et al. | |
| 5,863,293 A | 1/1999 | Richelsoph | |
| 5,879,350 A | 3/1999 | Sherman et al. | |
| 5,882,350 A | 3/1999 | Ralph et al. | |
| 5,885,285 A | 3/1999 | Simonson | |
| 5,885,286 A | 3/1999 | Sherman et al. | |
| 5,891,145 A | 4/1999 | Morrison et al. | |
| 5,954,725 A | 9/1999 | Sherman et al. | |
| 5,964,760 A | 10/1999 | Richelsoph | |
| 5,989,250 A | 11/1999 | Wagner et al. | |
| 6,010,503 A | 1/2000 | Richelsoph et al. | |
| 6,019,759 A | 2/2000 | Rogozinski | |
| 6,022,350 A | 2/2000 | Genem | |
| 6,053,917 A | 4/2000 | Sherman et al. | |
| 6,063,089 A | 5/2000 | Errico et al. | |
| 6,074,391 A | 6/2000 | Metz-Stavenhagen et al. | |
| 6,077,262 A | 6/2000 | Schläpfer et al. | |
| 6,090,111 A | 7/2000 | Nichols | |
| 6,132,430 A | 10/2000 | Wagner | |
| 6,132,434 A | 10/2000 | Sherman et al. | |
| 6,224,598 B1 | 5/2001 | Jackson | |
| 6,248,105 B1 | 6/2001 | Schläpfer et al. | |
| 6,280,442 B1 | 8/2001 | Barker et al. | |
| 6,287,311 B1 | 9/2001 | Sherman et al. | |
| 6,290,703 B1 | 9/2001 | Ganem | |
| 6,355,038 B1 | 3/2002 | Pisharodi | |
| 6,361,535 B2 | 3/2002 | Jackson | |
| 6,368,321 B1 | 4/2002 | Jackson | |
| 6,371,957 B1 | 4/2002 | Amrein et al. | |
| 6,416,515 B1 | 7/2002 | Wagner | |
| 6,440,132 B1 | 8/2002 | Jackson | |
| 6,451,021 B1 | 9/2002 | Ralph et al. | |
| 6,454,773 B1 | 9/2002 | Sherman et al. | |
| 6,458,132 B2 | 10/2002 | Choi | |
| 6,471,705 B1 | 10/2002 | Biedermann et al. | |
| 6,485,491 B1 | 11/2002 | Farris et al. | |
| 6,485,492 B1 | 11/2002 | Halm et al. | |
| 6,485,494 B1 * | 11/2002 | Haider | 606/73 |
| 6,520,963 B1 | 2/2003 | McKinley | |
| 6,524,315 B1 | 2/2003 | Selvitelli et al. | |
| 6,540,748 B2 * | 4/2003 | Lombardo | 606/61 |
| 6,540,749 B2 | 4/2003 | Schäfer et al. | |
| 6,547,790 B2 | 4/2003 | Harkey, III et al. | |
| 6,554,834 B1 | 4/2003 | Crozet et al. | |
| 6,562,040 B1 | 5/2003 | Wagner | |
| 6,565,565 B1 | 5/2003 | Yuan et al. | |
| 6,595,992 B1 | 7/2003 | Wagner et al. | |
| 6,613,050 B1 | 9/2003 | Wagner et al. | |
| 6,626,908 B2 * | 9/2003 | Cooper et al. | 606/61 |
| 6,641,586 B2 | 11/2003 | Varieur | |
| 6,660,004 B2 | 12/2003 | Barker et al. | |
| 6,660,005 B2 * | 12/2003 | Toyama et al. | 606/61 |
| 6,692,500 B2 * | 2/2004 | Reed | 606/73 |
| 6,733,502 B2 | 5/2004 | Altarac et al. | |
| 6,755,829 B1 * | 6/2004 | Bono et al. | 606/61 |
| 7,087,057 B2 * | 8/2006 | Konieczynski et al. | 606/73 |
| 2002/0120272 A1 | 8/2002 | Yuan et al. | |
| 2003/0125742 A1 | 7/2003 | Yuan et al. | |
| 2003/0167058 A1 | 9/2003 | Shulzas | |
| 2004/0193160 A1 | 9/2004 | Richelsoph | |
| 2006/0084981 A1 * | 4/2006 | Shluzas | 606/61 |

FOREIGN PATENT DOCUMENTS

| | | |
|---|---|---|
| EP | 0947174 A2 | 6/1999 |
| EP | 0947174 A3 | 9/2001 |

* cited by examiner

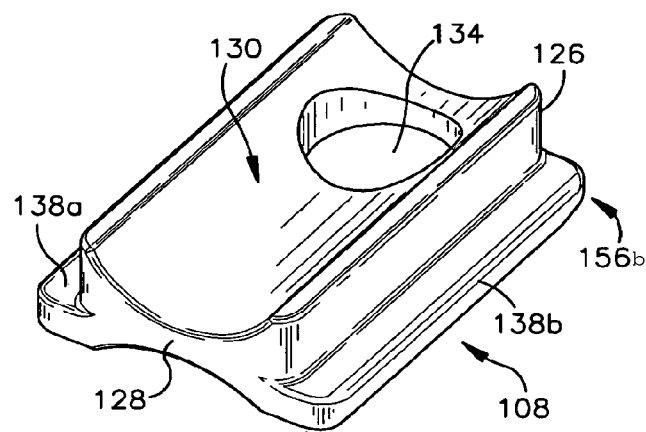
Figure 4A
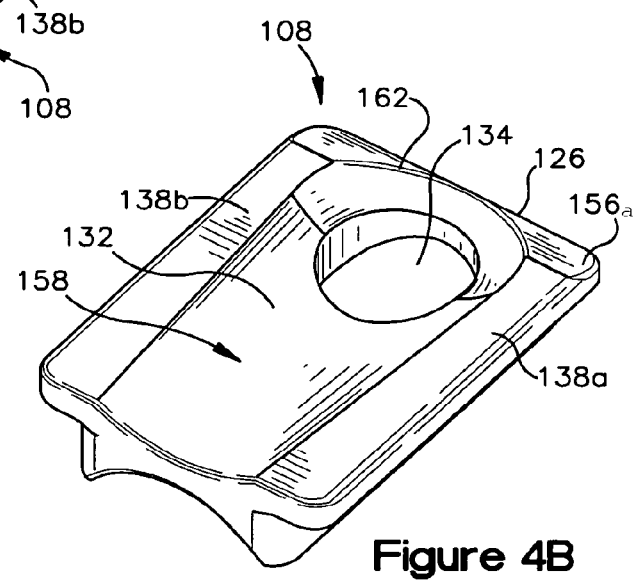
Figure 4B
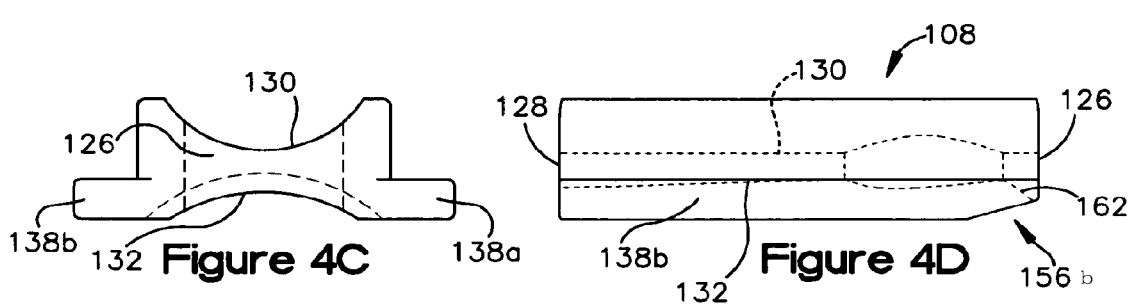
Figure 4C          Figure 4D

SPINAL FIXATION LOCKING MECHANISM

FIELD OF THE INVENTION

The present invention relates generally to prostheses for treating spinal pathologies, and more specifically to a bone interface anchor for holding a stabilization rod.

BACKGROUND OF THE INVENTION

Various methods of spinal immobilization have been used during this century in the treatment of spinal instability and displacement. The most common treatment for spinal stabilization is immobilization of the joint by surgical fusion, or arthrodesis. This has been known for almost a century. In many cases, however, pseudoarthrosis is a problem, particularly in cases involving fusion across the lumbosacral articulation and when more than two vertebrae are fused together. Early in the century, post operative external immobilization such as the use of splints and casts was the favored method of spinal fixation. As surgical techniques became more sophisticated, various methods of internal and external fixation were developed.

Internal fixation refers to therapeutic methods of stabilization that are wholly internal to the patient and include commonly known devices such as bone plates, screws, rods and pins. External fixation, in contrast, involves at least some portion of the stabilization device being located external to the patient's body. As surgical technologies and procedures became more advanced and the likelihood of infection decreased, internal fixation became the favored method of immobilization since it is less restrictive on the patient.

Internal fixation of the spine may be used to treat a variety of disorders including kyphosis, spondylolisthesis and rotation, segmental instability, such as disc degeneration and/or fracture caused by disease, trauma, congenital defects and tumor diseases.

One of the main challenges associated with spinal fixation is securing the fixation device to the spine without damaging the spinal cord. The pedicles of a vertebra are commonly used for fixation as they generally offer an area that is strong enough to hold the fixation device in place to fix the treatment area even when the patient suffers from degenerative instability such as osteoporosis. Early fixation devices involved the use of screws extending through the facets and into the pedicles.

Current fixation devices and hardware systems used internally for spinal fixation in modern surgical procedures are generally designed to meet one or more criteria, such as: providing rigidity as is indicated, generally along the long axis of the patient's spine; accommodating a broad variation in the size and shape of the spinal member with which it is used; having the capability of handling the stresses and strains to which the devices will be subjected resulting from movement of the spine; and providing easy surgical access during both implantation and removal of the implant.

Of these factors, the most difficult to achieve may very well be providing easy surgical access when the implant is being deployed and/or removed by surgeon. In particular, surgeons often wish to fit, test, adjust and refit fixation devices numerous times during a procedure in order to ensure that the device is optimally positioned. This is particularly important when dealing with the spinal column due to the risk of paralysis.

One example of a device designed as an attempt to meet the above-described criteria is disclosed in U.S. Pat. No. 5,466,237. The fixation device disclosed includes what is described as a variable position locking anchor having a bone screw and a seat.

The disclosed device uses a nut as a locking mechanism. As disclosed, the nut is tightened to the seat to compress an attached rod along a longitudinal axis of the screw, causing the screw to engage in mating contact with the seat and thereby locking the screw in place. In use, it is difficult to maintain proper positioning of the fixation device while tightening a nut or other such locking mechanism. Moreover, many existing fixation devices suffer from splaying apart of the sides of the seat of the fixation device when compressive force is used to locking a rod in position with a screw. The sides of the seat can splay apart and creates gaps in the fixation device and decreases its effectiveness. It would preferable if the fixation device was resistant to splaying.

It would be preferable if the screw could be locked without having to generate the necessary compressive force by tightening the nut or other such locking mechanism. It would also be preferable if the locking mechanism included a partial or preliminary lock for assisting the surgeon in fitting the implant prior to finally locking the implant in place. It would further be preferable if the locking mechanism was designed to prevent, or at the very least, minimize splaying of the various parts of the locking mechanism.

The present invention includes a novel fixation device that overcomes the disadvantages of the prior art.

BRIEF SUMMARY OF THE INVENTION

According to an aspect of the present invention, there is provided a locking mechanism configured to engage and lock a relative position of a bone fixation device and a relative position of a stabilization device. The locking mechanism comprises a seat having a bottom portion configured to receive the fixation device and prevent the fixation device from passing entirely therethrough, as well as a side portion configured to receive the stabilization device and a locking element between the fixation device and the stabilization device. The side portion of the seat is configured to receive the locking element such that receipt of the locking element causes locking of the relative positions of the fixation device and the stabilization device.

According to another aspect of the present invention, there is provided a locking mechanism configured to engage and lock a relative position of a bone fixation screw and a relative position of a rod. The locking mechanism comprises a tulip shape seat having a bottom portion configured to receive a fixation screw having a head and a shaft where the head is wider than the shaft. The bottom portion has a hole larger than the shaft and smaller than the head such that when a fixation screw is passed through the hole, the bottom portion engages the head. The tulip shape seat also has a side portion configured to receive the rod and a wedge between the rod and the fixation screw. The side portion of the tulip shape seat is configured to receive the wedge such that receipt of the wedge by the side portion of the tulip shape seat forces the fixation screw and the rod apart and causes locking of the relative positions of the fixation screw and the rod.

According to another aspect of the present invention, there is provided a method for locking the relative positions of a fixation device and a stabilization device comprising: fixing to bone a fixation device extending through a bottom portion of a seat; placing a stabilization device through a side portion of the seat; and slidingly engaging a locking element with the side portion of the seat between the stabilization device and the fixation device to cause locking of the relative positions of the fixation device and the stabilization device.

BRIEF DESCRIPTION OF THE DRAWINGS

FIG. 2A is a cross-sectional side view of the locking mechanism of the present invention with a fixation device and a stabilization device;

FIGS. 4A-D are top perspective, bottom perspective, front plan and side plan views of the locking element of the present invention;

DETAILED DESCRIPTION OF THE INVENTION

Figure 1:
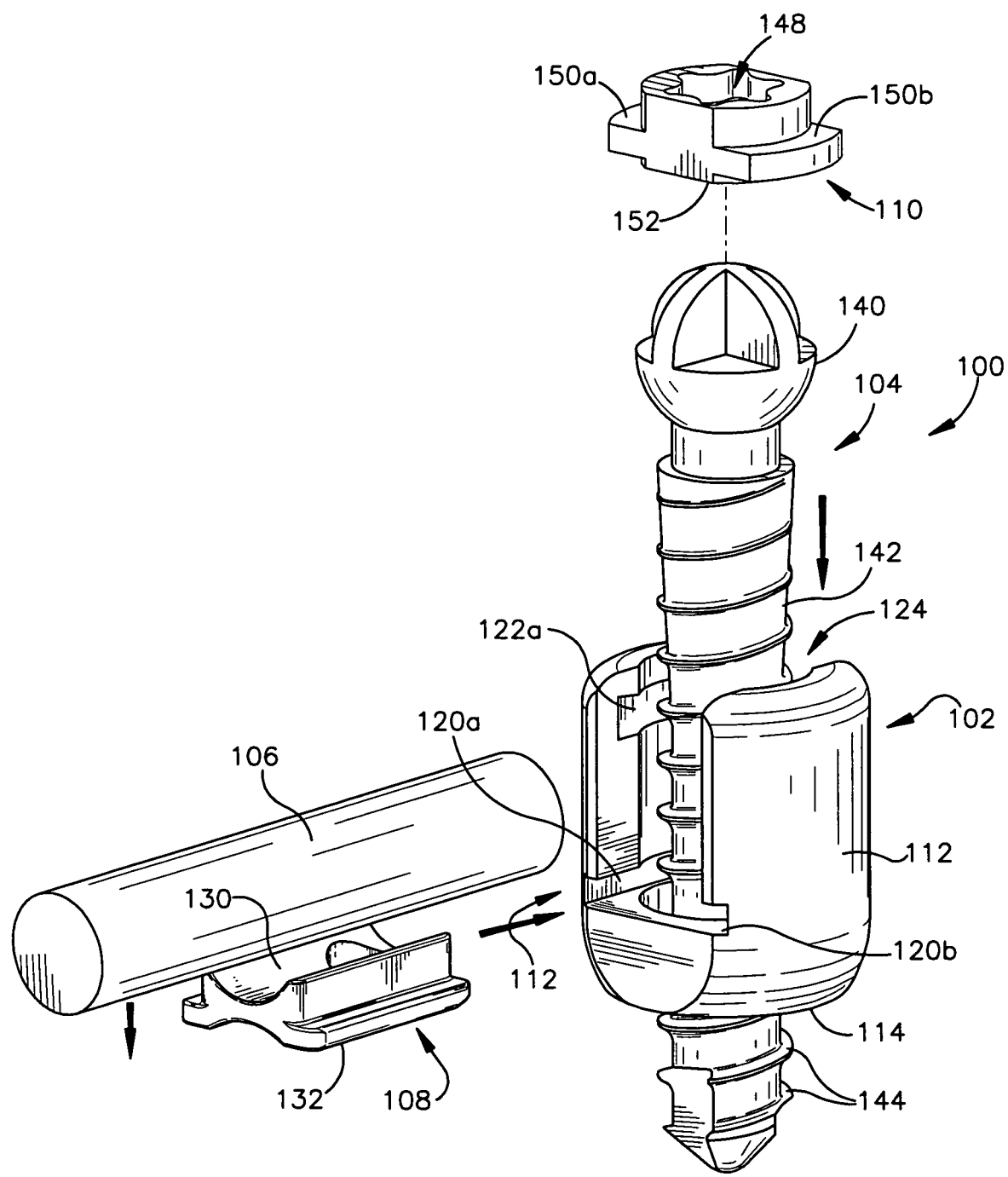
FIG. 1 is an exploded perspective view of the locking mechanism of the present invention with a fixation device and a stabilization device.
Figure 2C:
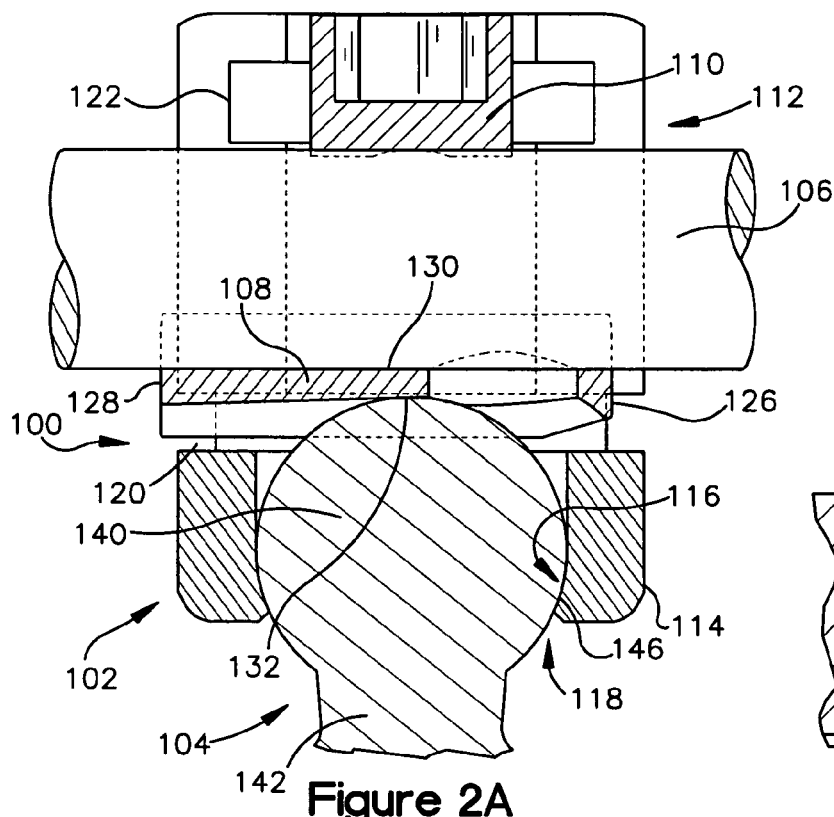
FIGS. 2C-D are cross-sectional front views of alternate retaining element and retaining groove configurations of the present invention.
Figure 2C:
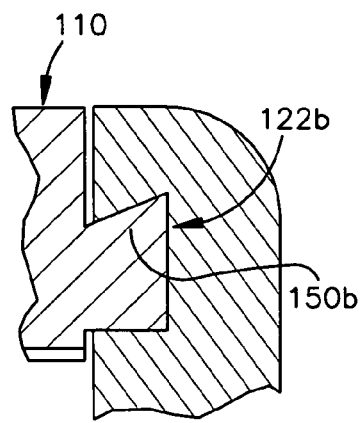
Figure 2B:
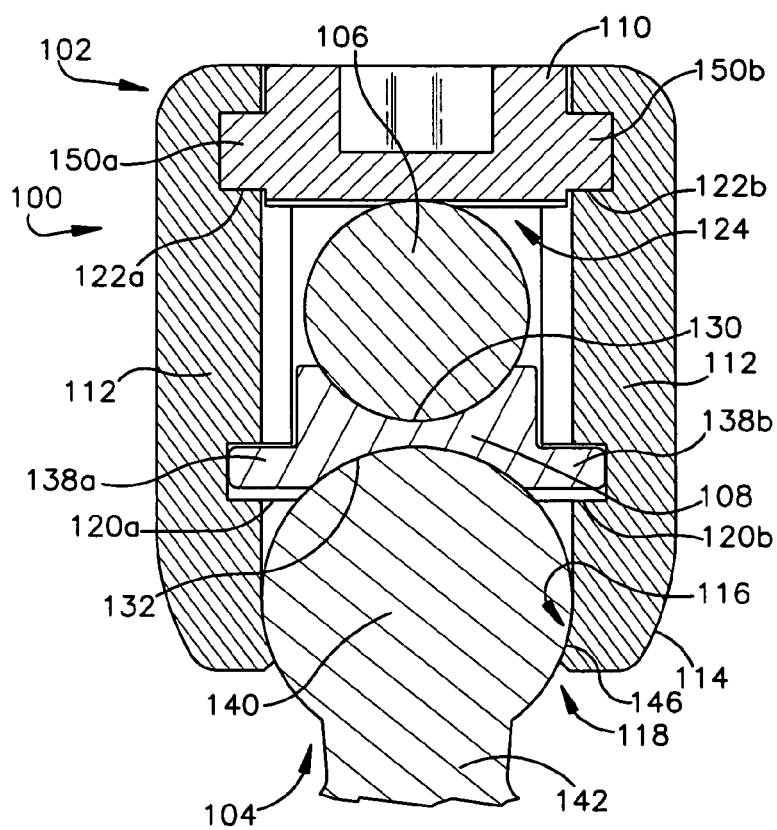
FIG. 2B is a cross-sectional front view of the locking mechanism of the present invention with a fixation device and a stabilization device.

Turning initially to FIGS. 1 and 2A-D, FIG. 1 shows an exploded perspective view of the locking mechanism of the present invention, and FIGS. 2A-B show cross sectional views of the locking mechanism of the present invention. The locking mechanism 100 is configured to engage and lock the relative position of a fixation device 104 with respect to the relative position of a stabilization device 106. The locking mechanism 100 includes a seat 102 and a locking element 108. The seat 102 includes a bottom portion 114 that is configured to receive the fixation device 104 such that the socket 116 of the bottom portion 114 engages part of the fixation device 104 and prevents the fixation device 104 from passing entirely therethrough.

Figure 5A:
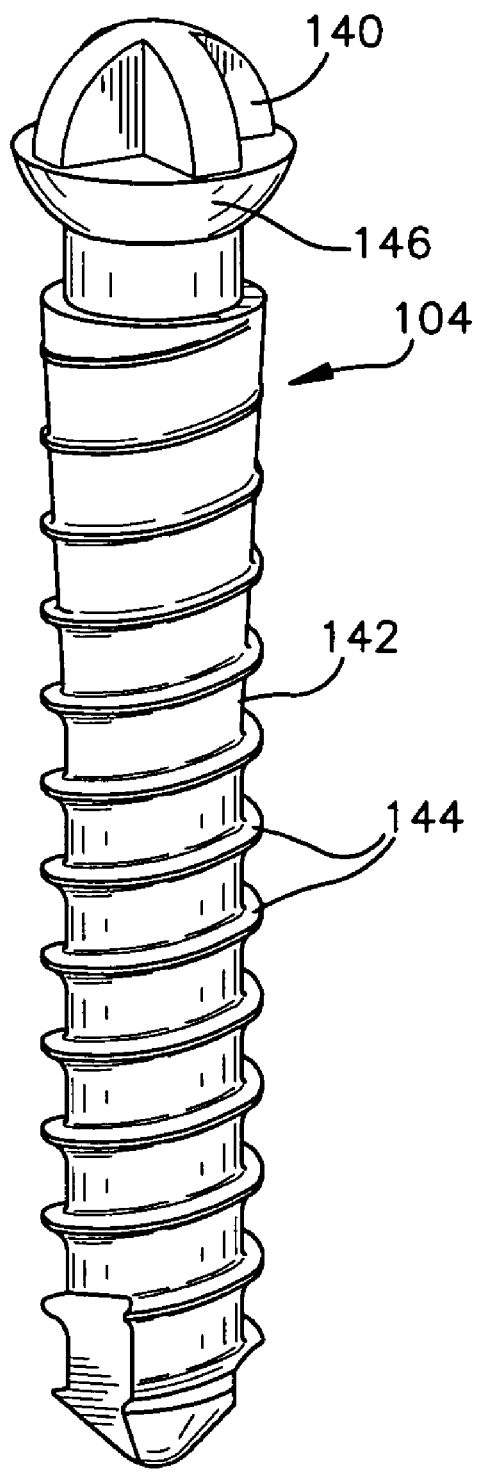
FIGS. 5A-B are perspective views of exemplary fixation devices with which the present invention can be used.
Figure 5B:
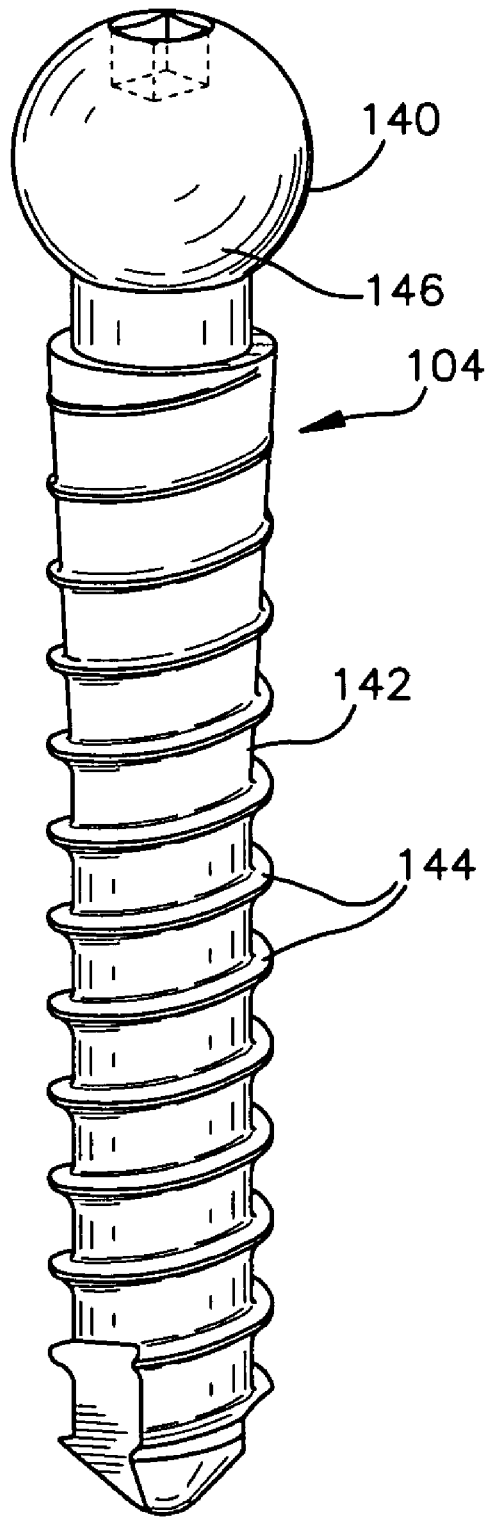

The fixation device 104 may be, for example, a screw having a head 140 and shaft 142 with threads 144. Examples of fixation devices 104 are shown in FIGS. 5A and 5B. In order to prevent the fixation device 104 from passing entirely through the seat 102, the seat 102 preferably includes a hole 118 that is larger than the shaft 142 and smaller than the head 140. When the fixation device 104 is forced toward the bottom portion 114 of the seat 102, the socket 116 of the bottom portion 114 of the seat 102 engages the head 140 of the fixation device 104. In addition, the socket 116 of the bottom portion 114 may be tapered to receive and engage the fixation device 104.

The seat 102 also includes a side portion 112 that is configured to receive the stabilization device 106 and a locking element 108. The stabilization device 106 may be, for example, a rod, and the side portion 112 of the seat 102 may include a channel 124 for receiving the stabilization device 106.

Figure 2D:
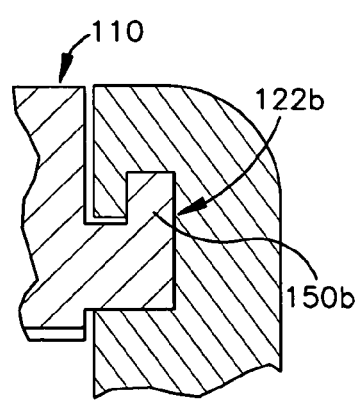
Figure 3A:
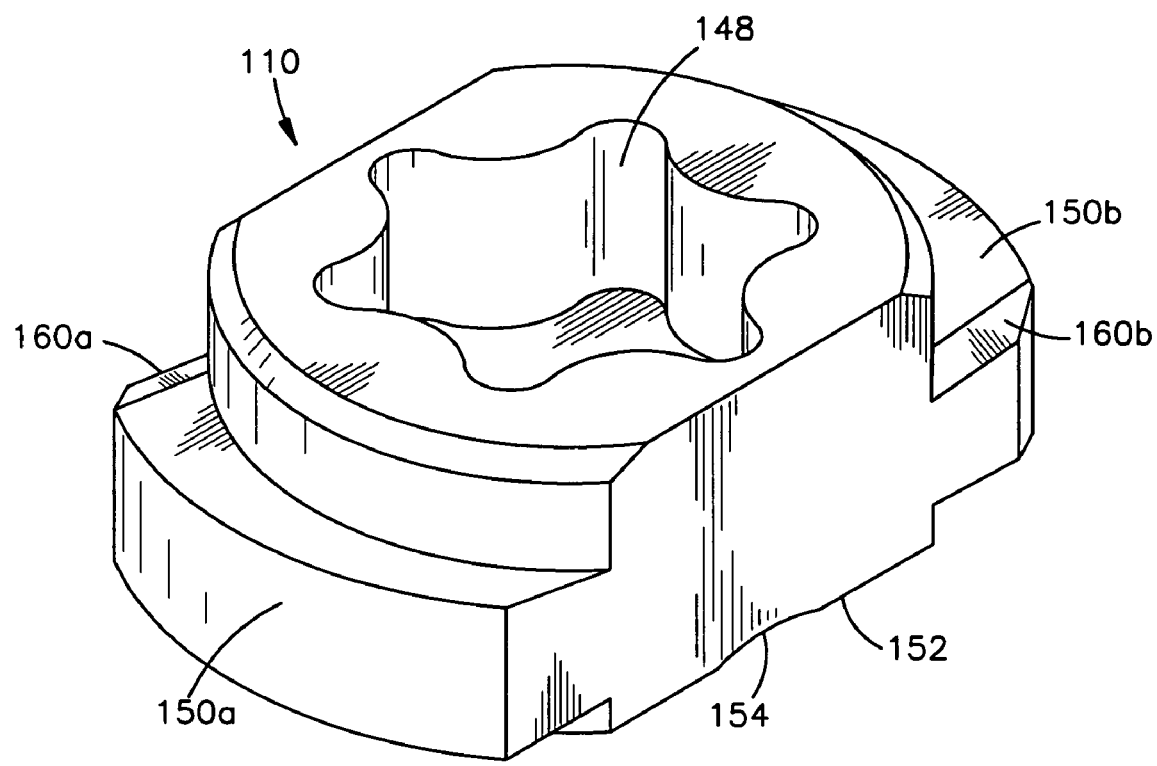
FIGS. 3A-D are top perspective, bottom perspective, top plan and side plan views of a retaining element according to the present invention.
Figure 3B:
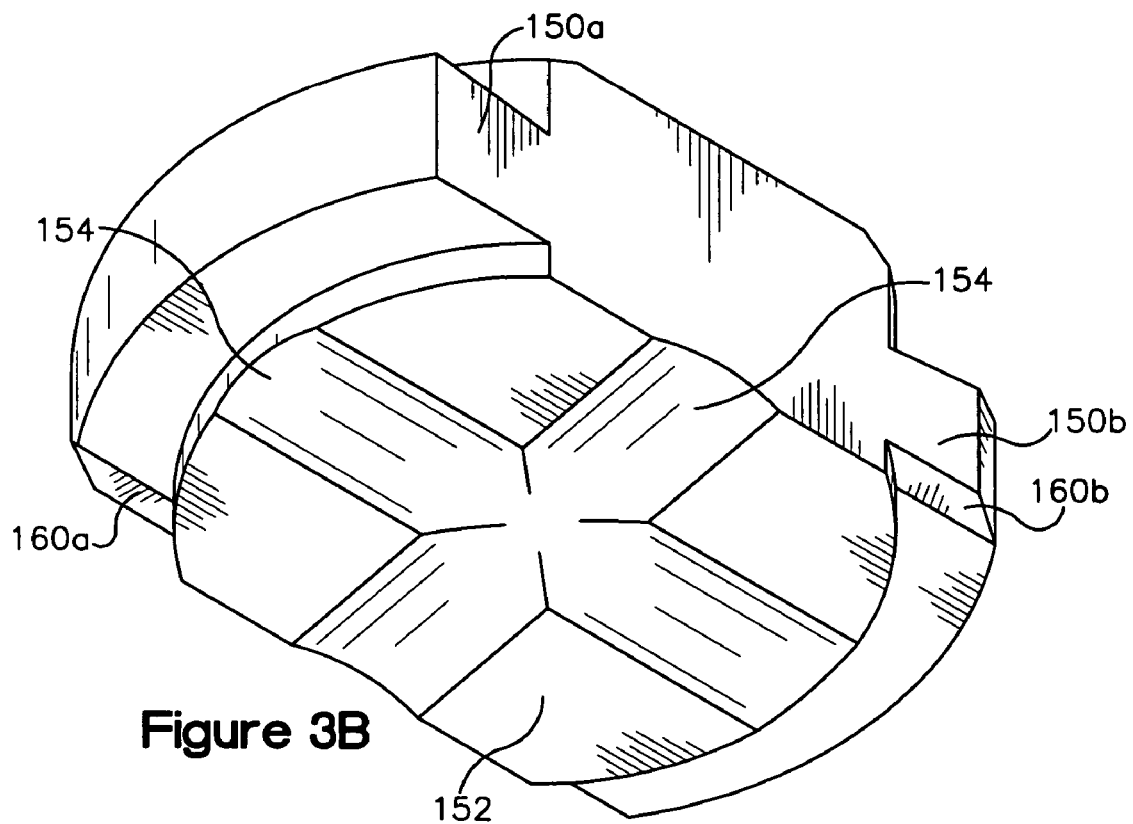
Figure 3C:
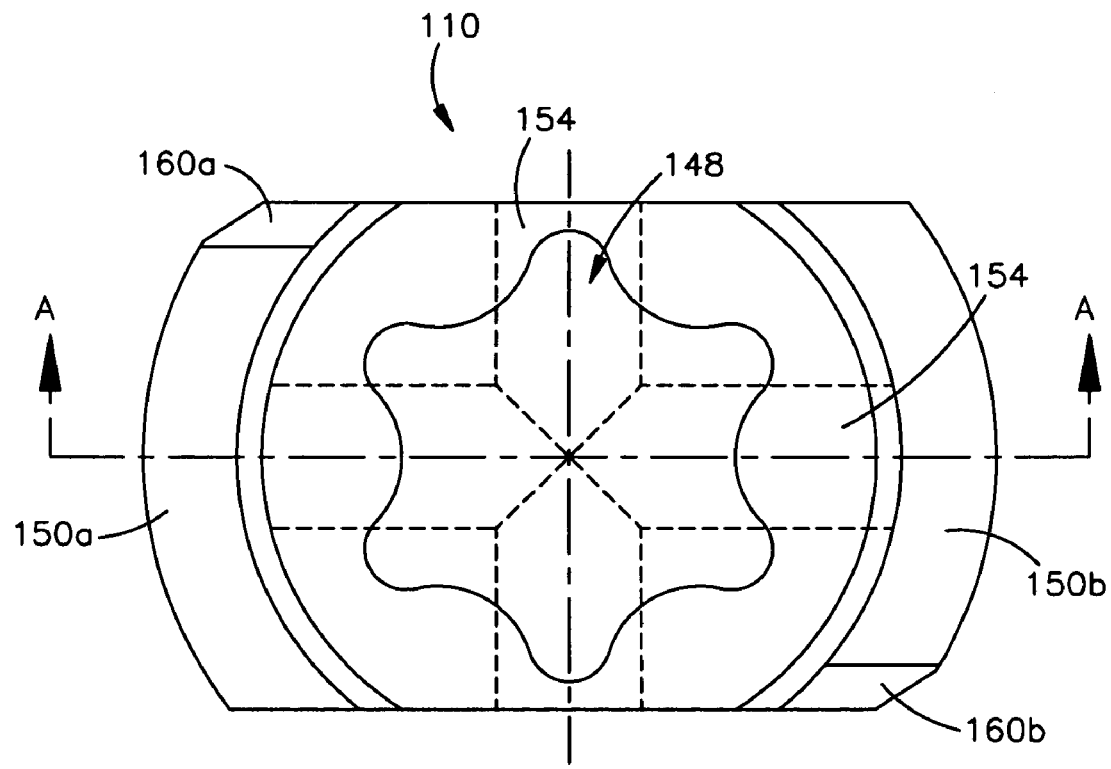
Figure 3D:
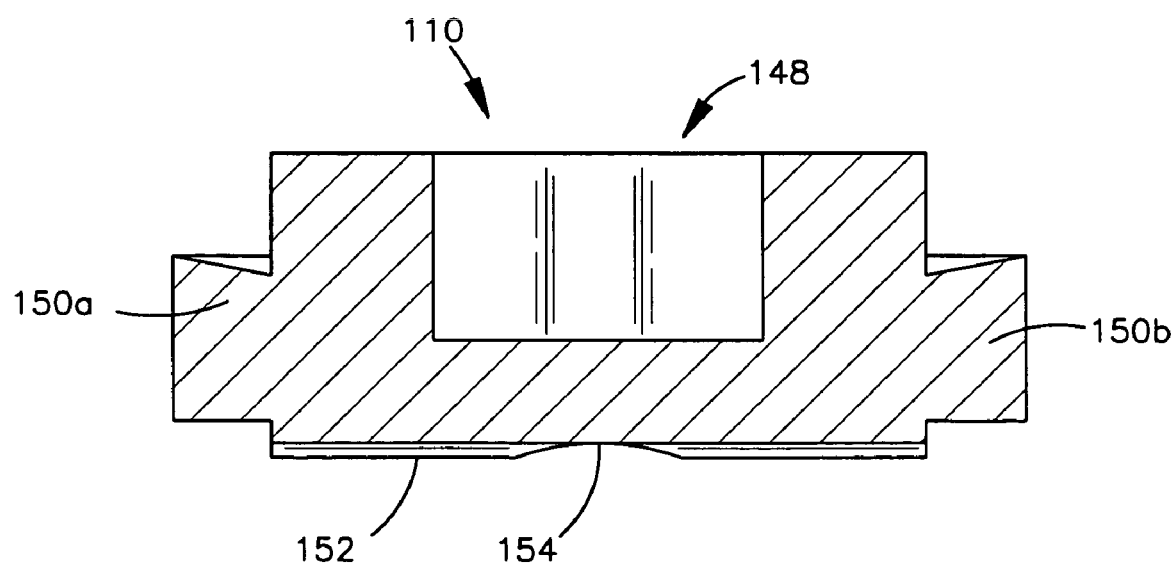

The locking mechanism 100 may also include a retaining element 110 that is configured to engage the seat 102 and the stabilization device 106 such that the retaining element 110 acts to limit movement of the stabilization device 106 away from the fixation device 104. The retaining element 110 and seat 102 may be, for example, slidably engageable, rotatably engageable and/or snapably engageable. Accordingly, the seat 102 may include a retaining groove 122 for receiving the retaining element 110. In addition, the seat 102 may also include a lip to reduce splaying of the sides of the seat 102. FIGS. 2C-D show different types of configurations of retaining grooves 122 and retaining elements 110 that can be used to help prevent splaying of the sides 112 of the seat 102.

The locking element 108 is configured for engagement with the side portion 112 of the seat 102 to cause locking of the relative positions of the fixation device 104 and the stabilization device 106. The locking element 108 is preferably engageable with the side portion 112 of the seat 102 between the fixation device 104 and the stabilization device 106 such that the locking element 108 causes the fixation device 104 and the stabilization device 106 to be forced apart.

To facilitate engagement with the locking element 108, the side portion 112 of the seat 102 may include at least one locking groove 120 configured to accept a slidably engageable locking element 108. The locking groove 120 may be positioned in the side portion 112 of the seat 102 such that the locking element 108 is generally parallel to a longitudinal axis of the stabilization device 106 when engaged with the seat 102. The locking element 108 may be partially engageable with the seat 102 such that the fixation device 104 and the stabilization device 106 are caused to become partially locked so as to facilitate placement and alignment of the fixation device 104 and the stabilization device 106. Once the locking element 108 is fully engaged, repositioning may be more difficult.

The locking element 108 is preferably disengageable from the seat 102 once partially engaged with the seat 102 so as to facilitate a change in placement or alignment of the fixation device 104 and/or the stabilization device 106. In order to make the locking element 108 more readily disengageable from the seat 102, the locking element 108 may be longer than the width of the seat 102 so that when the locking element 108 and seat 102 are fully engaged, the locking element 108 protrudes from the side portion 112 of the seat 102. The locking element 108 may also be configured such that the locking element 108 permits access to the fixation device 104 when the locking element 108 is partially engaged with the seat 102.

The locking element 108 may include, for example, a wedge, a normally open biased structure or an inflatable structure. Preferably, the locking element 108 has a fixation device side 132 and stabilization device side 130 wherein the surface of at least one of the fixation device side 132 or stabilization device side 130 is a ramped surface. It will also be understood that the present invention may utilize a locking element 108 that is not ramped at all. In addition, the stabilization device side 130 may be contoured to interact with the contour of the stabilization device 106 and the fixation device side 132 may be contoured to interact with the contour of the fixation device 108.

Turning now to FIGS. 2A and 2B, the locking mechanism 100 of the present invention is illustrated in greater detail. FIG. 2A is a cross-sectional side view of the locking mechanism 100 of the present invention with a fixation device 104 and a stabilization device 106. FIG. 2B is a cross-sectional front view of the locking mechanism 100 of the present invention with a fixation device 104 and a stabilization device 106.

The locking mechanism 100 includes a seat 102 and a locking element 108 for engaging a fixation device 104 and a stabilization device 106. The locking mechanism 100 may also include a retaining element 110 to assist in engagement. Each of the seat 102, fixation device 104, stabilization device 106, locking element 108 and retaining element 110 may be made from a variety of materials known in the art and preferably are made from biocompatible materials when the locking mechanism 100 is used for bone fixation. Such materials include, but are not limited to, titanium, titanium alloys (e.g. titanium/aluminum/vanadium (Ti/Al/V) alloys), cobalt-chromium alloys, stainless steel, ceramics (alumina ceramic, zirconia ceramic, yttria zirconia ceramic, etc.), high strength polymers (e.g. PEEK, PEKK, etc.), pyrolytic carbon, tantalum, carbon composite materials and combinations thereof. Some materials are more appropriate for fixation surfaces, such as cobalt-chromium alloys, titanium, and (Ti/Al/V) alloys, but any material known in the art for use with fixation surfaces can be used in the present invention. Such materials are commonly used in bone fixation and the like. Preferably, the materials are rigid and in one embodiment, the seat 102, fixation device 104, stabilization device 106, locking element 108 and retaining element 110 are all made from Ti/Al/V alloys, such as Ti/6Al/4V ELI.

While one of skill in the art will recognize that fixation devices 104 other than a screw can be used without departing from the scope of the present invention, a screw is shown and described herein to illustrate the engagement of the fixation device 104 and the seat 102, as well as the method for locking the relative positions of a fixation device 104 and a stabilization device 106. Furthermore, various types of screws may be used. Two exemplary types of screws are illustrated in FIGS. 5A and 5B.

The size of the seat 102 may be similar to that of prior art devices. For example, the height of seat 102 may range from about 0.4 inch to about 1 inch. In one embodiment, the height of the seat 102 ranges from about 0.588 inch to about 0.598 inch. Also, the width of seat 102 may range from about 0.25 inch to about 1 inch. In one embodiment, the width of the seat 102 ranges from about 0.405 inch to about 0.415 inch.

The seat 102 has a side portion 112 and a bottom portion 114. The bottom portion 114 may be tapered as shown in FIG. 2B and includes a socket 116 and a hole 118. Because the general shape of the type of seat 102 illustrated in FIGS. 1 and 2A-B somewhat resembles a tulip flower, this type of seat 102 is often referred to as a "tulip" by those skilled in the art. The socket 116 is preferably sized to accept a fixation device 104, such as a screw, and the hole 118 is preferably sized to prevent the fixation device 104 from passing entirely therethrough. The hole 118 is preferably located at the bottom of the seat 102.

The socket 116 is configured for locking engagement of the fixation device 104, or more specifically, the engagement surface 146 of the head 140 of the fixation device 104. In order to facilitate locking engagement, the surface of the socket 116 may include a rough or knurled surface and/or a surface fixation mechanism, such as ridges, grooves, bumps, pips, or the like. In addition, an engagement surface 146 of the fixation device 104 may have a similar surface.

The seat 102 also includes a channel 124 in the side portion 112 for receiving the stabilization device 106, such as a rod or a dynamic stabilization element. While a channel 124 is preferred for receiving the stabilization device 106, it will be understood by those skilled in the art that an aperture in the side portion 112 could also receive the stabilization device, though a seat 102 with an aperture may be more cumbersome to deploy during surgery as a surgeon would have to place the stabilization device 106 through the aperture instead of placing the stabilization device in the channel 124. Using a channel 124 to receive the stabilization device 106 provides greater flexibility for a surgeon.

After placement of the stabilization device 106 within the channel 124, it is desirable to retain the stabilization device 106 within the channel 124 so that a locking element, such as locking element 108, can fix the position of the stabilization device 106. Accordingly, the side portion 112 of the seat 102 also includes retaining grooves 122a and 122b configured to receive a retaining element 110. The retaining grooves 122a and 122b are located at least above the centerline of the stabilization element 106 in the channel 124 and may be located above the top of the stabilization element 106 in the channel 124. When the locking mechanism 100 is used for spinal fixation, "above" means posterior with respect to the patient and "below" means anterior with respect to the patient. Thus, the bottom portion 114 of the seat 102 is anterior with respect to the patient and the fixation device 104 and stabilization device 106 are received by the seat 102 as the fixation device 104 and stabilization device 106 are moved in a posterior to anterior direction.

The retaining element 110 is thus engaged with the retaining grooves 122a and 122b of the side portion 1124 of the seat 102 to keep the stabilization device 106 within the channel 124. The retaining element 110 and the seat 102 may be slidably engageable, rotatably engageable, and/or snapably engageable. In the embodiment disclosed in FIGS. 1, 2A-B and 3A-D, the retaining element 110 and the seat 102 are rotatably engageable. It will be understood by those of skill in the art that the primary purpose of the retaining element 110 is not to force the stabilization device 106 into engagement with the fixation device 104. Rather, the primary purpose of the retaining element 110 is to prevent the stabilization device 106 from being forced out of the channel 124 by the locking element 108. In other words, the retaining element 110 is not screwed down to apply increasing force to the stabilization device 106 in order to engage and lock the stabilization device 106 and fixation device 104. Without the locking element 108, the retaining element 110 by itself is not designed to lock the fixation device 104 and engagement device 106.

The side portion 112 of the seat 102 is also configured to receive a locking element 108 that is configured to engage the side portion 112 of the seat 102. In the exemplary embodiment of FIGS. 1, 2A-B and 3A-D, the locking element is slidably engageable with locking grooves 120a and 120b of the side portion 112 of the seat 102. In this embodiment, the locking grooves 120a and 120b are below the centerline of the stabilization element 106 and above the centerline of the head 140 of the fixation element 104.

It will be understood by one of skill in the art that while FIGS. 2A and 2B illustrate a seat 102 configured to receive a locking element 108 having a linear axis generally parallel to the linear axis of the stabilization device 106, the seat 102 may also be configured to receive a locking element 108 that has a linear axis that is generally not parallel to the linear axis of the stabilization device 106. For example, the linear axis of the locking element 108 may have an axis that is generally orthogonal, generally parallel, or anywhere in between, with respect to the axis of the stabilization device 106. In other words, the locking element 108 may be received by the seat 102 at any location around the seat 102.

When the locking element 108 engages the locking grooves 120a and 120b, the locking element 108 forces the fixation device 104 and the stabilization device 106 apart and causes the locking of the relative positions of the fixation device 104 and stabilization device 106. In addition, the locking element 108 may be longer than the width of the seat 102 so that once fully engaged with the locking grooves 120a and 120b, the locking element 108 protrudes from the side portion 112 of the seat 102. This may be advantageous for certain uses of the locking mechanism 100 of the present invention, such as to enable a surgeon to more easily engage and disengage the locking element 108, either partially or fully. In addition, the size of the portion of the locking element 108 that protrudes may be visible to a surgeon and act as a visible indicator of the level of engagement.

As shown in FIGS. 4A-D, the locking element 108 is configured for placement between a fixation device 104 and a stabilization device 106 and may be in the form of a wedge having a front side 126 and a back side 128. The locking element 108 also includes a fixation device side 132 and a stabilization device side 130. The surface of the fixation device side 132 may be ramped from the front side 126 to the back side 128. The surface of the stabilization device side 130 may also be ramped from the front side 126 to the back side 128. In other words, either one or both of the surfaces of the fixation device side 132 and stabilization device side 130 may be ramped. In addition, both of the surfaces of the fixation device side 132 and stabilization device side 130 may not be ramped at all.

The degree of incline of the ramp may vary, but generally ranges from about 0.5 to about 6 degrees. In one embodiment, the degree of include ranges from about 1.5 to about 4 degrees.

In addition, the surface of the fixation device side 132 and/or the stabilization device side 130 may be relatively smooth, as opposed to other engagement surfaces of the locking mechanism 100. In addition, the locking element 108 may be made from a titanium alloy and the surfaces of the fixation device side 132 and/or stabilization device side 130 may have a rough or knurled surface and/or a surface fixation mechanism, such as ridges, grooves, bumps, pips, or the like to increase the surface coefficient of friction. For example, the stabilization device side 130 or fixation device side 132 may be roughened by aluminum oxide blasting.

One of skill in the art will understand that other surface treatments may also be used on the surfaces of the fixation device side 132 and stabilization device side 130. One of skill in the art will also understand that any of the surfaces of the locking mechanism 100, and/or any of the surfaces of the fixation device 104, and/or any of the surfaces of the stabilization device 106 may also be surface treated.

The fixation device side 132 may be contoured to improve engagement with the fixation device 104. The contour may increase the area over which the locking element 108 and fixation device 104 are engaged. For example, if the locking mechanism 100 is being used to engage a fixation device 104 with a generally spherical head 140, the fixation device side 132 may be contoured such that it includes a channel with a curvature that approximates the curvature of the head 140. Similarly, the stabilization device side 130 may be contoured to increase the area over which the locking element 108 and stabilization device 106 are engaged. Where the stabilization device 106 is a rod, the stabilization device side 130 may be contoured such that it includes a channel with a curvature that approximates the curvature of the outer surface of the rod. It will understood by those in the art that the contour may alternatively decrease in the area over which the locking element 108 and fixation device 104 are engaged.

Figure 6A:
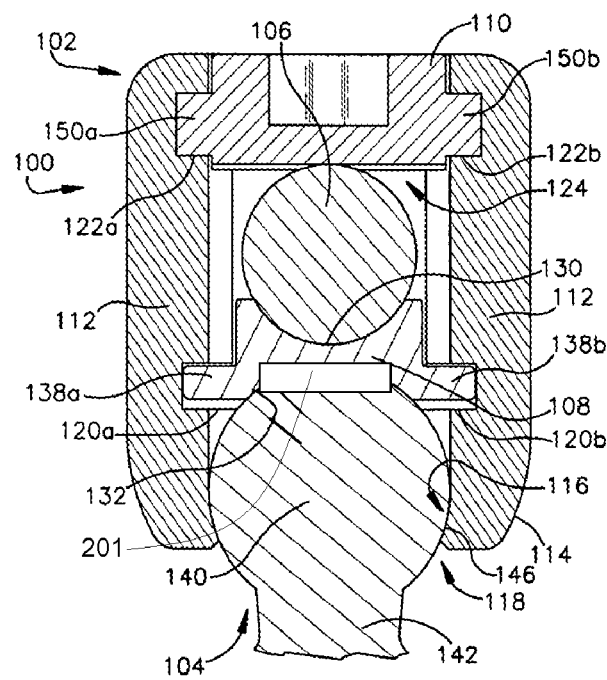
FIGS. 6A-B are cross-sectional front views of the locking mechanism with alternate locking elements.

Also, the fixation device side 132 may be designed so that it enhances the fixation of the fixation device to a target. For example, the fixation device side 132 may include interdigitating fingers 201, shown in FIG. 6A, ridges or other mechanism for increasing the interaction between the fixation device side 132 and the fixation device 104, such as a screw.

In the exemplary embodiment of FIGS. 1, 2A-B and 4A-D, the locking element 108 is slidably engageable with locking grooves 120a and 120b of the side portion 112 of the seat 102. Accordingly, the locking element 108 also includes edges 138a and 138b configured for sliding engagement with the locking grooves 120a and 120b. The edges 138a and 138b may each include a nose lead-in 156a and 156b to facilitate the initial placement of the edges 138a and 138b in the locking grooves 120a and 120b, respectively.

In addition, the locking element 108 may include an access hole 134 for providing access to the fixation device 104 after the locking element 108 is partially engaged with the side portion 112 of the seat 102. The access hole 134 may also provide access for adjusting or placing a fixation device 104 where a locking element 108 is placed prior to placement or adjustment of the fixation device 104. The access hole 134 is preferably offset toward the front side 126 of the locking element 108. Thus, when the locking element 108 is only partially engaged, the access hole 134 is more directly located above the fixation device 104 than it would otherwise be if the access hole 134 were located in the center of the locking element 108. Thus, when the locking element 108 is partially engaged with the side portion 112, a drive mechanism can pass through the access hole 134 to exert drive force on the fixation device 104.

Also, the locking element 108 may have a self-retaining mechanism, such as a ridge, on the fixation device side 132 to act as a self-retaining mechanism. The ridge 162 may also be on the stabilization device side 130. Preferably, the ridge is located toward the front side 126 of the locking element 108 so that when the locking element 108 is engaged with seat, the ridge helps prevent the locking element 108 from withdrawing.

Further, the locking element 108 may be narrower in width at the access hole 134 so that a lesser engagement of the locking element 108 and the fixation device 104 exists when the access hole 134 is located above the fixation device 104. Further, the locking element 108 may have a taper 158 on the fixation device side 132, the stabilization device side 130, or both. Preferably, the locking element 108 has a taper 158 on the fixation device side 132 to assist the locking element 108 with engagement of the fixation device 104.

The locking element 108 may also be configured so that locking element 108 is locked when fully engaged with the side portion 112. To facilitate locking, the locking element 108 may include a latch, catch, tooth or the like to act as an anchor preventing the locking mechanism 100 from being retracted once the locking mechanism 108 has been fully engaged.

In addition, the locking element 108 and seat 102 may include a feedback mechanism to indicate the engagement of the locking element 108 and seat 102. For example, the locking element 108 may be color coded or have ridges or bumps designed to mate with ridges or bumps on the seat 102 so that, for example, a surgeon could feel the interaction of the mating ridges or bumps in order to determine the level of engagement of the locking element 108 with the seat 102.

In order for a locking element 108 that is placed between the fixation device 104 and stabilization device 106 to lock the relative positions of the fixation device 104 and stabilization device 106, the locking mechanism 100 preferably also includes a retaining element 110 that limits upward movement of the stabilization device 106 caused by force exerted on it by the locking element 108. It will be understood by one of skill in the art that other types of retaining elements 110 may be used. For example, the side portion 112 of the seat 102 could act as a retaining element 110 where the stabilization device 106 is inserted into the seat 102 through a hole in the side portion 112 of the seat 102. Any other type of retaining element 110 may also be used.

Figure 6B:
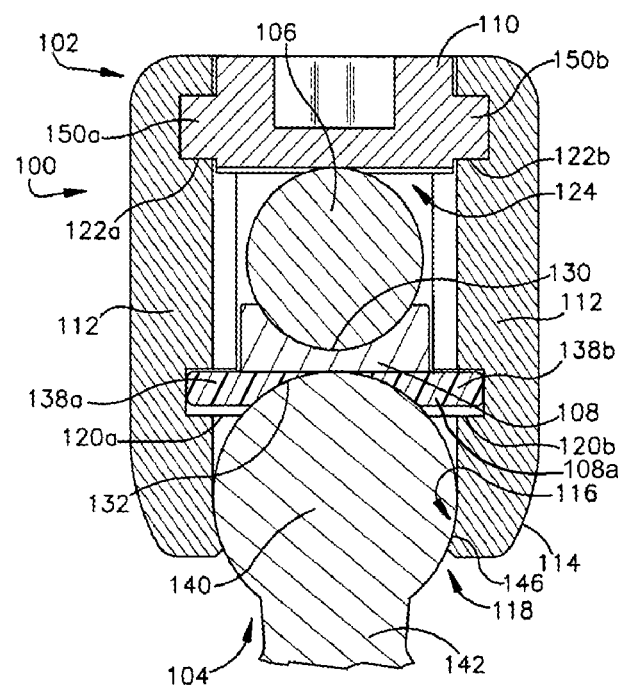

It will also be understood by those skilled in the art that an intermediate element may be used between the locking element 108 and either or both the fixation device 104 and stabilization device 106 may departing from the scope of the present invention. For example, the intermediate element may be a spacer 108a, shown in FIG. 6B, between the locking element 108 and the fixation device 104. The spacer may thus be configured to have contoured surface, and/or interdigitating fingers, like those described with reference to the fixation device surface 132 of the locking element 108. Similarly, in intermediate element between the locking element 108 and stabilization device 106 may have a surface similar to the stabilization device surface 130.

FIGS. 1, 2A-B and 3A-D illustrate perspective, top plan and side plan views of an exemplary retaining element 110 according to the present invention. As described above, the retaining element 110 keeps the stabilization device 106 in the channel 124 and prevents the stabilization device 106 from moving away from the locking element 108 when the locking element 108 is engaged the side portion 112 of the seat 102 to force the stabilization device 106 and fixation device 104 apart. Also as described above, the retaining element 110 may be a cap like that illustrated in FIGS. 3A-D. In addition, the retaining element 110 may be, for example, hingedly connected to the seat 102, either vertically or horizontally. Also, the retaining element 110 could, for example, be incorporated into the side portion 112 of the seat 102, such as where the stabilization device 106 is prevented from moving away from the fixation device 104 by the upper edge of a hole in the side portion 112 through which the stabilization element 106 runs.

In the specific embodiment of FIGS. 1, 2A-B and 3A-D, the retaining element 110 is in the form of a cap. The retaining element 110 is preferably longer in one direction than in the other such that when the retaining element 110 is rotated 90 degrees, it engages the retaining grooves 122a and 122b of the side portion 112 of the seat 102. As shown, the retaining element 110 includes a turning element 148 that is configured to receive a tool that facilitates rotating the retaining element 110 into engagement with the retaining grooves 122a and 122b. Specifically, the retaining element 110 includes wings 150a and 150b configured to engage the retaining grooves 122a and 122b. The wings 150a and 150b each include a nose 160a and 160b, respectively, on the edge of the wings 150a and 150b to facilitate engagement with the retaining grooves 122a and 122b. The retaining element 110 is preferably engageable with the retaining grooves 122a and 122b by placing the retaining element 110 adjacent to the retaining grooves 122a and 122b and then rotating the retaining element 90 degrees clockwise so that the noses 160a and 160b engage the retaining grooves 122a and 122b, thereby facilitating the engagement of the wings 150a and 150b with the retaining grooves 122a and 122b.

The retaining element 110 also includes a stabilization device surface 152 that prevents the stabilization device 106 from moving up the channel 124 when the wings 150a and 150b are engaged with the retaining grooves 122a and 122b. The stabilization device surface 152 may also include a contour 154 that approximates the outer surface of the stabilization device 106. The contour 154 may include, for example, at least one channel running across the stabilization device side 1524 of the retaining element 110.

In addition, the retaining element 110 and seat 102 may include a feedback mechanism to indicate the engagement of the retaining element 110 and seat 102. For example, the retaining element 110 may have ridges or bumps designed to mate with ridges or bumps on the seat 102 so that, for example, a surgeon could feel the interaction of the mating ridges or bumps in order to determine the level of engagement of the retaining element 110 with the seat 102.

It will be understood by those skilled in the art that the specific embodiment of the retaining element illustrated in the accompanying figures is only one of a variety of types of retaining elements that could be used without departing from the scope of the present invention. For example, the retaining element 110 could be slidingly engageable with the retaining grooves 122a and 122b in a linear manner. Those skilled in the art will understand that the specific shapes and types of the grooves 120a, 120b, 122a and 122b may vary substantially. For example, the retaining groove 122a may include miniature slots within the retaining groove 122a to interact with small bumps on the wing 150a so that it is apparent when the wing 150a and retaining groove 122a are properly engaged. Similarly, the wings 150a and 150b may have a surface with small ridges to create increased friction between the wings 150a and 150b and the retaining grooves 122a and 122b to help prevent the retaining element 110 from disengaging.

Such surfaces may be rough or knurled and/or include at least one surface fixation mechanism, such as ridges, grooves, bumps, pips, or the like to increase the surface coefficient of friction. For example, the surfaces may be roughened by aluminum oxide blasting. One of skill in the art will understand that other surface treatments may also be used.

In addition as shown in FIGS. 2C-D, the retaining grooves 122a and 122b and the wings 150a and 150b may be configured to prevent the splaying apart of the sides 112 of the seat 102. Many configurations may be apparent to one of skill in the art. For example, the wings 150a and 150b and retaining grooves 122a and 122b may be configured such that the retaining grooves 122a and 122b have top surfaces that form acute angles with the side surfaces of the retaining grooves 122a and 122b. In addition, the wings 150a and 150b and retaining grooves 122a and 122b may have locking lips, as shown in FIG. 2D.

In use, the fixation mechanism 100 of the present invention provides a convenient method for engaging and locking a relative position of a fixation device 104 and a stabilization device 106. According to one aspect of the present invention, the fixation device 104 is passed through the bottom portion 114 of the seat 102 and then fixed to a target, such as a spinal vertebra or other bone. A stabilization device 106 is then placed through a side portion 112 of the seat 102. In a specific embodiment, the stabilization device is placed in a channel 124. Following placement of the stabilization device 106, a locking element 108 is slidably engaged with the side portion 112 of the seat 102 between the fixation device 104 and the stabilization device 106 to cause locking of the relative positions of the fixation device 104 and the stabilization device 106. In addition, the retaining element 110 may be engaged with the seat following the placement of the stabilization device 106 and before fully engaging the locking element 108.

In addition, the fixation mechanism 100 may permit partial locking of the fixation device 104 prior to placing the stabilization device 106. For example, a locking element 108 can be partially engaged with the fixation device 104 either before or after placing the stabilization element 106. In addition, the locking element 108 may include a hole that permits access to the fixation device 104 by a drive mechanism to fix the fixation device 104 to a target, such as a vertebra or bone. In this instance, the locking element 108 may be partially engaged before fixing the fixation device 104 to a target.

The locking mechanism 100 also permits readjustment of the stabilization device 106 prior to full engagement of the locking element 108. Accordingly, the locking element 108 can be partially engaged, then the fixation device 104 can be fixed to a target, then the stabilization device 106 can be positioned and readjusted as necessary before fully engaging the locking element 108 to fix the relative positions of the fixation device 104 and the stabilization device 106. Also, the locking element 108 may be partially engaged following fixation of the fixation device 104 to a target. In addition, the locking element 108 may not be partially engaged at all, but simply fully engaged once the fixation device 104 and stabilization device 106 are appropriately placed.

While the present invention has been described in association with exemplary embodiments, the described embodiments are to be considered in all respects as illustrative and not restrictive. Such other features, aspects, variations, modifications, and substitution of equivalents may be made without departing from the spirit and scope of this invention which is intended to be limited only by the scope of the following claims. Also, it will be appreciated that features and parts illustrated in one embodiment may be used, or may be applicable, in the same or in a similar way in other embodiments.

What is claimed is:

1. A locking mechanism configured to engage and lock a relative position of a bone fixation device and a relative position of a stabilization device, the locking mechanism having a seat comprising:
   a bottom portion configured to receive the fixation device and prevent the fixation device from passing entirely therethrough; and
   a side portion configured to receive the stabilization device and a locking element between the fixation device and the stabilization device;
   wherein receipt of the locking element by the side portion causes locking of the relative positions of the fixation device and the stabilization device; and
   wherein the locking element comprises a rectangular shape and is longer than the width of the seat such that when the locking element and the seat are engaged, the locking element protrudes from the side portion.

2. A locking mechanism configured to engage and lock a relative position of a bone fixation screw and a relative position of a rod, the locking mechanism having a tulip shape seat comprising:
   a bottom portion configured to receive a fixation screw having a head and a shaft where the head is wider than the shaft, the bottom portion having a hole larger than the shaft and smaller than the head such that when a fixation screw is passed through the hole, the bottom portion engages the head; and
   a side portion configured to receive the rod and a rectangular shape wedge between the rod and the fixation screw;
   wherein receipt of the wedge by the side portion of the tulip shape seat forces the fixation screw and the rod apart and causes locking of the relative positions of the fixation screw and the rod; and
   wherein the wedge is longer than the width of the seat such that when the wedge and the seat are engaged, the wedge protrudes from the side portion.

3. A method for locking the relative positions of a fixation device and a stabilization device comprising:
   fixing to bone a fixation device extending through a bottom portion of a seat;
   partially engaging a locking element with a side portion of the seat prior to placing a stabilization device;
   placing the stabilization device in the side portion of the seat;
   engaging a retaining element with the seat prior to fully engaging the locking element with the side portion of the seat; and
   slidingly engaging the locking element with the side portion of the seat between the stabilization device and the fixation device to cause locking of the relative positions of the fixation device and the stabilization device.

4. The method of claim 3 further comprising adjusting the retaining element prior to fully engaging the locking element with the side portion of the seat.

5. A locking mechanism configured to engage and lock a relative position of a bone fixation device and a relative position of a stabilization device, the locking mechanism comprising:
   a seat comprising a bottom portion configured to receive the fixation device and prevent the fixation device from passing entirely therethrough and a side portion comprising an opening shaped and dimensioned to receive the stabilization device;
   a retaining element shaped and dimensioned to engage the side portion of the seat so as to retain the stabilization device within said seat and to limit movement of the stabilization device away from the fixation device;
   a locking element shaped and dimensioned to be slidably inserted through said opening after said retaining element has engaged the side portion and to engage the side portion so as to be positioned between the fixation device and the stabilization device; and
   wherein said insertion and positioning of the locking element between the fixation device and the stabilization device forces said fixation device and said stabilization device apart and causes locking of the relative positions of the fixation device and the stabilization device within said seat.

6. The locking mechanism of claim 5 further comprising a feedback mechanism to indicate engagement of at least one of the retaining element or the locking element.

7. The locking mechanism of claim 5 wherein the retaining element and the seat are at least one of: slidably engageable, rotatably engageable or snapably engageable.

8. The seat of claim 7 comprising a retaining groove for receiving the retaining element and a lip to reduce splaying of the sides of the seat.

9. The locking mechanism of claim 5 wherein the seat and locking element are engageable at multiple locations along the side portion of the seat.

10. The locking mechanism of claim 5 wherein the fixation device comprises a screw having a shaft and a head and the bottom portion of the seat comprises a hole that is larger than the shaft and smaller than the head.

11. The locking mechanism of claim 5 wherein said opening of the side portion of the seat comprises a channel.

12. The locking mechanism of claim 5 wherein the stabilization device comprises a rod.

13. The locking mechanism of claim 5 wherein the bottom portion comprises a socket tapered to receive and engage the fixation device.

14. The locking mechanism of claim 5 wherein the side portion of the seat comprises a locking groove for engaging the locking element.

15. The locking mechanism of claim 14 wherein the locking element comprises at least one of: a wedge, a normally open biased structure or an inflatable structure.

16. The locking mechanism of claim 15 wherein the locking element comprises a wedge having a fixation device side and stabilization device side wherein a surface of at least one of the fixation device side or stabilization device side is a ramped surface.

17. The locking mechanism of claim 5 wherein the side portion of the seat is configured to receive the locking element such that the locking element is generally parallel to a longitudinal axis of the stabilization device when engaged with the seat.

18. The locking mechanism of claim 5 wherein the locking element is partially engageable with the seat such that the fixation device and the stabilization device are caused to become partially locked so as to facilitate placement and alignment of the fixation device and the stabilization device.

19. The locking mechanism of claim 18 wherein the locking element is disengageable once partially engaged with the seat so as to facilitate a change in placement or alignment of at least one of the fixation device or the stabilization device.

20. The locking mechanism of claim 5 wherein the locking element is further configured to permit access to the fixation device after the locking element is at least partially engaged with the seat.

21. The locking mechanism of claim 5 wherein the locking element comprises a stabilization device side that is contoured to interact with a contour of the stabilization device.

22. The locking mechanism of claim 5 wherein the locking element comprises a fixation device side that is contoured to interact with a contour of the fixation device.

23. The locking mechanism of claim 5 wherein the locking element comprises interdigitating fingers for engaging the fixation device.

24. The locking mechanism of claim 5 further comprising a spacer between the locking element and the fixation device to cooperatively transfer force from the locking element to the fixation device.

25. The locking mechanism of claim 24 wherein at least one side of the spacer comprises at least one of: a contoured surface or interdigitating fingers.

26. The locking mechanism of claim 5 wherein said locking element comprises a rectangular shape.

* * * * *